(12) United States Patent
Desantis et al.

(10) Patent No.: US 10,350,433 B2
(45) Date of Patent: Jul. 16, 2019

(54) LAYER STRUCTURE FOR EPIDERMAL RADIONUCLIDE THERAPY

(75) Inventors: Maria Desantis, Rome (IT); Oliver Buck, Bayerisch Gmain (DE); Cesidio Cipriani, Rome (IT)

(73) Assignee: Oncobeta International GmbH, Ravensburg (DE)

( * ) Notice: Subject to any disclaimer, the term of this patent is extended or adjusted under 35 U.S.C. 154(b) by 672 days.

(21) Appl. No.: 14/123,578

(22) PCT Filed: May 16, 2012

(86) PCT No.: PCT/EP2012/059108
§ 371 (c)(1),
(2), (4) Date: Feb. 4, 2014

(87) PCT Pub. No.: WO2012/168047
PCT Pub. Date: Dec. 13, 2012

(65) Prior Publication Data
US 2014/0296609 A1    Oct. 2, 2014

(30) Foreign Application Priority Data
Jun. 6, 2011 (DE) .......... 10 2011 050 848

(51) Int. Cl.
*A61N 5/10* (2006.01)

(52) U.S. Cl.
CPC .................. *A61N 5/1029* (2013.01)

(58) Field of Classification Search
CPC .. A61N 5/1029; A61N 5/1028; A61K 5/1279; A61L 26/0076
See application file for complete search history.

(56) References Cited

U.S. PATENT DOCUMENTS

| | | | |
|---|---|---|---|
| 4,946,435 A | 8/1990 | Suthanthiran et al. | |
| 6,350,226 B1 | 2/2002 | Fishcell et al. | |
| 6,749,553 B2* | 6/2004 | Brauckman | A61N 5/1027 600/3 |
| 2006/0025516 A1* | 2/2006 | Shalaby | A61L 26/0014 524/556 |
| 2007/0055147 A1* | 3/2007 | Dalzell | A61L 31/18 600/431 |
| 2007/0244203 A1* | 10/2007 | Raul | A61K 8/06 514/770 |
| 2008/0132467 A1* | 6/2008 | Lauto | A61L 24/001 514/55 |
| 2010/0278762 A1* | 11/2010 | Kaplan | A61K 8/8152 424/59 |
| 2013/0218060 A1* | 8/2013 | Bushby | A61F 5/013 602/21 |

FOREIGN PATENT DOCUMENTS

| | | |
|---|---|---|
| DE | 3133909 | 3/1983 |
| EP | 2098251 | 9/2009 |
| FR | 1332345 | 7/1963 |

* cited by examiner

*Primary Examiner* — Christine H Matthews
*Assistant Examiner* — Joshua Daryl D Lannu
(74) *Attorney, Agent, or Firm* — Lewis Kohn & Walker LLP; David M. Kohn; Kari Moyer-Henry

(57) ABSTRACT

Disclosed is a layer structure for epidermal radionuclide therapy (brachytherapy) of a patient comprising, from a patient's view, a proximal adherent layer for applying the layer structure on the skin surface to be treated of a patient; a flexible, transparent carrier layer that from a patient's view is located in a distal direction on the adherent layer; and at least one radionuclide-containing emission layer located on the carrier layer, the adherent layer and the carrier layer with regard to their components and thickness being formed such that they are essentially transparent for β and γ radiation. The layer structure is suited particularly for radiotherapeutic treatment of the basal-cell carcinoma (BCC) and the squamous cell carcinoma (SCC). With the aid of the layer structure, geometrically complex skin lesions caused by a tumor, as occurring e.g. on the outer edge of the auricle, may be treated easily.

10 Claims, No Drawings

LAYER STRUCTURE FOR EPIDERMAL RADIONUCLIDE THERAPY

This application is a United States National Stage Application claiming the benefit of priority under 35 U.S.C. 371 from International Patent Application No. PCT/EP2012/059108 filed May 16, 2012, which claims the benefit of priority from German Patent Application Serial No. DE 10 2011 050 848.1 filed Jun. 6, 2011, the entire contents of which are herein incorporated by reference.

The present invention relates to a layer structure for epidermal radionuclide therapy of a patient comprising:

from a patient's view, a proximal adherent layer for applying the layer structure on a patient's skin surface, an adherent layer consisting of a skin cream and/or skin gel being excluded;

a flexible, transparent carrier layer that from a patient's view is located in a distal direction on top of the adherent layer; and at least one radionuclide-containing emission layer located on the carrier layer;

wherein the adherent layer and the carrier layer with regard to their components and thickness are formed such that they are essentially transparent for $\alpha$, $\beta$ and $\gamma$ radiation, wherein the adherent layer is formed on the skin surface prior to assembling the layer structure, and wherein the adherent layer is formed of a synthetic film sprayable onto the skin surface, characterized in that the synthetic film is formed of a liquid bandage on the basis of polyurethanes, polyacrylates, especially poly(butyl methacrylate, methyl methacrylate); or 2-octyl cyanoacrylate; that the carrier layer foil is selected from the group consisting of: polyurethane foil, polyamide foil, polyolefin foil, in particular polyethylene and polypropylene foil, and that the emission layer is a water-based polyacrylate matrix including homogenously spread $^{188}$rhenium sulfide, particularly $^{188}Re_2S_7$.

Skin cancer is the most frequent type of cancer occurring in humans and in some countries pertains to up to 50% of all types of tumors. Among all tumors existing in humans the basal-cell carcinoma (BCC) is the most frequent cancer occurring within the white population. Approximately 80% of the cases of skin cancer are basal-cell carcinoma. BCC is a slowly growing locally invasive malign epidermal skin tumor that tends to infiltrate and destroy the fascia. However, metastatic spread is very rare. At the beginning of the disease the tumor is a superficial translucent knot of wax or pearl grey color. The most advanced types frequently exhibit ulcerations, in particular in their center regions and on their edges. Basal-cell carcinoma may occur on any location of the body, however, 90% of the lesions appear in the face and on the head. The BCC most frequently occurs in light-skinned middle or upper age patients who indicate an exposure to ultraviolet radiation in their anamnesis, however, basal-cell carcinoma may also occur in a basal-cell nevus as so-called Gorlin syndrome. Due to the depletion of the ozone layer, Australia has the largest occurrence of BCC worldwide; in some areas, the tumor incidence per year is up to 2%.

If a patient has developed a BCC there is a significantly increased risk of further basal-cell carcinoma developing in other locations of the body. Studies have shown that the basal-cell carcinoma may develop from multipotent cells in the basal layer or from follicles of the skin. However, different histological and clinicopathological types of the basal-cell carcinoma exist, but the existing diagnostic methods do not provide sufficient information with regard to the characteristics of the tumor.

The second most common skin tumor in addition to the basal-cell carcinoma is the squamous cell carcinoma (SCC). The SCC is a malign epithelial disease with the morphological characteristics of squamous cell differentiation without additional features suggesting other differentiated tissue. It may occur on any region of the body and may also develop on the lips, the vulva and the penis. It was often observed that the squamous cell carcinoma arises as a result of scars on account of burns or ulcers and appears as a superficial slightly bleeding lesion. Sometimes, an ulceration with thick crater-like edges develops, while in other cases, the lesion is covered with horny layers.

Other varieties of this type of tumor arise from the superficial layer and are known in particular as Bowen dermatosis and correspond to a squamous cell carcinoma in situ, which then possibly only after further years may lead to a breach through the basal layer and penetration of the corium and thus to a keratinizing squamous cell carcinoma. A precancerosis for the squamous cell carcinoma also is the so-called erythroplasia of Queyrat which constitutes a superficial type of in situ SCC of male and female genital areas as well as of lips and mouth. Erythroplasia is characterized by alterations that are comparatively sharply confined, little infiltrated, wet shining or erosive.

A particular type of the squamous cell carcinoma is keratoacanthoma, which is a skin tumor probably originating from hair follicles.

Finally, as sun-induced damage, also actinic keratosis occurs, also referred to as solar keratosis, which in dermatology these days is considered as beginning form of a carcinoma in situ.

As was already mentioned above, the squamous cell carcinoma is the second most common form of skin cancer with more than 200,000 new cases per year in the U.S.A. Not surprisingly, the disease occurs most frequently in Australia, an age-corrected incidence of 1332 cases per 100,000 inhabitants for males and 755 cases per 100,000 inhabitants for females having been calculated. In European countries the annual incidence of the squamous cell carcinoma amounts to 25 cases per 100,000 inhabitants. The squamous cell carcinoma of the skin is able to metastasize into the regional lymphatic glands and frequently relapses locally.

The occurrence of BCC and SCC rises with increasing age, starting approximately at the age of 30 and having a peak at the age of 65 to 70. The diseases occur more frequently in males than in females. Both types of tumors most frequently occur in the face, on the neck area, the hairless scalp, hands, shoulders, arms and on the back. The edges of the ears and the lower lip are hit particularly often by these types of cancer. The clinical appearances and morphologies of the two types of tumors are different and include nodule-forming, cystically ulcerated (rodent ulcer), superficial, morphoic (sclerosing), keratotic and pigmented varieties.

Ulceration particularly frequently occurs in large tumors that have existed for a long time, or in aggressive lesions. The risk factors for both types of tumors include exposure to the sun, exposure to ionizing radiation, exposure to arsenic, tar derivates, and UV radiation. It was also ascertained that specific predisposing factors play a role, such as immunosuppression, physical characteristics, skin complexion, red or blonde hairs and light eye color.

While the basal cell carcinoma is rather characterized by non-aggressive behavior, which is due to its comparatively low metastasizing rate of approximately 0.03 to 0.6% (however, metastases were described in the subcutaneous tissue, the bones, the lung, the liver and the lymphatic glands in the throat), the squamous cell carcinoma exhibits a clearly more aggressive course and its metastasizing potential is clearly increased and amounts to approximately 2 to 5%. Due to a solely macroscopic and morphological examination of lesions by an experienced dermatologist that is quite difficult to perform, a correct diagnosis is of fundamental importance. Such diagnosis, however, is only made possible through microscopic, histological and cytological examination which enables exact characterization and classification. Tissue samples may be taken by surgical excision or through biopsy using suitable biopsy punches. Sometimes a simple cytological examination of the cicatrized lesion suffices to confirm a suspected diagnosis. Dermatoscopic epiluminescence, which in large skin areas is used for the diagnosis of pigmented lesions, allows for the observation and characterization of features and the assessment of the vascular pathways within the lesion. As a rule, the observation of neoangiogenesis which are a characteristic of cancerous lesions, provides useful hints to assessing the extension and depth of the lesion. Due to the high risk of metastatic dissemination exact time-based observation of the patient is absolutely required.

Clinical examinations require a whole-body examination of the skin, palpation of the surgically treated areas, and an examination of the skin between primary tumor areas and revulsive lymphatic glands for in transit metastatic spread. Regional lymphatic glands should be palpated for lymphadenopathy and suspicious enlargements of the lymphatic glands should be examined by way of a biopsy or imaging methods or both. Imaging techniques that are particularly useful are the use of a computer tomogram or a computer tomogram in combination with positron emission tomography. Examinations using magnetic resonance provide the best resolution for tumors in the soft tissue, particularly in the head and neck area, and should be considered for screening metastases that may occur in those areas. Should there be suspicious lymphatic glands, monitoring of lymphatic gland localization and lymphoscintigraphy by way of $^{99m}$Tc-colloid prior to and after a therapy is to be considered in all suspected cases. Characteristics of primary tumors which may evolve into metastatic squamous cell carcinoma, include a surface area of >120 mm$^2$, an invasion depth of >3.2 mm, and an invasion into underlying adipose, muscular or bone tissue.

The primary means of choice a priori is surgical intervention, edges of 2 to 4 mm for nodular, well-defined tumors up to a size of 2 cm being recommended. For tumors larger than 2 cm, excision with an edge of 1 cm or more is generally proposed, particularly in case of tumors with aggressive behavior.

As a surgical technique, Mobs surgery has turned out to be the most promising method for curing while at the same time preserving healthy tissue. The method consists in a progressive histological real-time examination of the tissue sections of the lesion during surgery until healthy tissue is reached.

In all cases in which tumors occur in areas that are difficult to access by surgical intervention, such as, for example, ears, nose and eye lids, the esthetic and functional results of surgical excision often are very unsatisfactory. If the lesion is rather large and the healthy skin remaining does not suffice for satisfactory surgical suture, it is necessary to take measures of plastic and reconstructive surgery, skin grafts (usually of the lower limbs or of the gluteus skin) being unavoidable.

The cosmetic result of such measures, however, quite often is not satisfactory. In case a relapse within the transplanted skin occurs treatment of the lesions becomes extremely problematic.

For both types of tumors there are standard therapies such as curettage and electric desiccation; surgery, cryosurgery and intralesional interferon therapy often are suggested to patients.

Meanwhile, also newer topical therapies are available for treatment of selected cases, such as, for example, tumors occurring in critical regions or in inoperable patients that suffer from other systemic diseases such as cardiomyopathy, pulmonary insufficiency, etc., so that a surgical intervention under general anesthesia is contraindicated. Those forms of therapy include the treatment with Imiquimod, an antiviral drug and immunomodulator, which is used for the treatment of superficial BCC, actinic keratosis and genital warts (*Condylomata acuminata*). Tazarotene, a retinoid, which in general is used for the topical treatment of psoriasis, was proposed for the local treatment of BCC. Moreover, a photodynamic therapy was proposed which includes the application of a tumor-localizing photosensitive agent and subsequent activation thereof with visible light so as to cause a selective destruction of the tumor. The use of an Imiquimod cream as an effective option for the treatment of superficial and nodular basal cell carcinoma exhibited a rate of success of 89.5% with a sequence check of 39 months on average (Vun, Y, Siller G, Australas J Dermatol. 2006, August; 47(3): 169-71). The use of a photodynamic therapy with Porfimer sodium likewise was described.

Moreover, photodynamic therapies using meso-tetra hydroxyphenyl chlorines (m-THPC) are known from the prior art.

All of the above-indicated methods of medical treatment are used for the treatment of small, superficial non-recurring BCC, but are not indicated for the treatment of nodular, cystic, infiltrative and morphoic varieties of the basal cell carcinoma.

Moreover, in the prior art attempts were made of treating BCC using photon irradiation with doses of 20 to 73 Gy as single or multiple treatment. In this treatment method, in 95% of cases of stage I and II carcinoma, no relapses occurred within a period of five years. Thus, the success of a radiation therapy with regard to its cure rates may provide comparable results as Mohs micrographic surgery, which in those kinds of tumors generally is considered as "gold standard" treatment.

Irradiation using conventional methods, in particular radiotherapy using external X-rays or γ-rays, due to the penetrating power of the photons, cannot be recommended for the treatment of tumors in those areas where irradiation can be very harmful, e.g. to the face and eyes. Moreover, radiotherapy of the squamous cell carcinoma with X-rays and γ irradiation also is not suited as treatment promising success.

A first very promising approach for the therapy of the basal cell carcinoma and the squamous cell carcinoma is described in Sedda A F, Rossi G, Cipriani C, Carrozzo A M and Donati T, 2008: Dermatological high-dose-rate brachytherapy for the treatment of basal and squamous cell carcinoma, Clinical and Experimental Dermatology, 33, 745-749, as well as in EP 2 098 251 A1.

The prior art indicated describes a therapeutic method for the basal cell carcinoma and the squamous cell carcinoma in which radioactive β rays emitting isotopes are used, particularly $^{188}$Re.

In the described method, the skin lesion to be treated is coated with a thin layer of a barrier cream and on the barrier cream a radioactive matrix of $^{188}Re_2S_7$ in form of a colloid which is thoroughly mixed with a synthetic acrylic resin, is applied onto the skin cream layer.

The polyacrylate layer hardens without essential shrinkage and, depending on the treatment scheme, is left between 15 minutes and 3 hours on the lesion to be treated.

Subsequently, the hardened $^{188}$rhenium acrylic resin dispersion is removed again manually from the lesion.

In so doing, $^{188}$Re isotopes have turned out to be particularly useful as $^{188}$Re is a mixed β-γ-emitter that has a half-life period of approximately 16.98 hours. The emitted β particles have a maximum energy of approximately 2.12 MeV and an average energy of 764 KeV and thus are therapeutically active only over a short distance. The portion of γ-rays is about 15% of the radiation intensity and its energy is approximately 155 KeV.

Moreover, γ-radiation is excellently suited for detecting possible radioactive contaminations with $^{188}$Re.

According to EP 2 098 451 A1 it turned out during examinations that the penetration depth of β-radiation into the epidermis is approximately 200 to 600 µm, which, of course, depends on histological conditions. The activity of the β emitter isotopes which were used in the therapy in accordance with EP 2 098 451 A1, was within a range of $3.7 \times 10^{-2}$ Gbq to 1.85 Gbq in case of larger lesions. In addition to $^{188}$Re also compounds of $^{90}$Y, $^{32}$P and $^{166}$Ho were used.

In a patient base of 200 histologically ascertained diagnoses of BCC or SCC, as a rule in 85% of the treated patients, a single treatment sufficed for full clinical remission which started after 3-5 months.

According to a follow-up study of four years on average, an overall rate of successful cures of up to 100% was achieved.

Consequently, brachytherapy with β radiation and $^{188}$Re in particular, is a promising therapeutic approach in such BCC and SCC lesions that surgically are very difficult to handle and with cosmetically disturbing effects.

However, as the dose required for treatment of a specific lesion has to be calculated very exactly and as the lesions moreover geometrically are often formed in a complex manner, a different filling of barrier cream resulted on account of the depth of the lesion to be treated varying from location to location, which led to local dependence of the intensity of β radiation and hence to β exposition, as the radiation is weakened more strongly in case of a larger amount of barrier cream than in areas of the lesion that are flatter and consequently include less barrier cream or even exhibit elevating portions.

Moreover, a further problem resulted from the removal of the radioactive polyacrylate matrix from the skin surface of a patient as instruments had to interfere in the cream layer between the polyacrylate layer and the skin surface, this sometimes resulting in cracks in the radioactive layer with possible slight radioactive contamination of the cream layer.

This led to extensive follow-up treatments in which the lesion had to be fully decontaminated, which, on the one hand, delayed curing and, on the other hand, involved further inconveniences to a patient.

Based on the prior art in accordance with EP 2 089 251 A1, it is therefore an object of the present invention to substantially safeguard uniform radiation over the entire lesion thereby avoiding varying diminutions of β radiation in the area of skin lesions while ensuring at the same time that the radioactive layer may be fully removed easily from the skin surface of a patient without any contamination.

The object is solved by the features of the present invention.

The invention particularly relates to a layer structure for epidermal radionuclide therapy of a patient, comprising:
from a patient's view, a proximal adherent layer for applying the layer structure on a patient's skin surface to be treated, an adherent layer consisting of a skin cream and/or skin gel being excluded;
a flexible, transparent carrier layer that from a patient's view is located in a distal direction on top of the adherent layer; and
at least one radionuclide-containing emission layer located on the carrier layer;
wherein the adherent layer and the carrier layer with regard to their components and thickness are formed such that they are transparent for γ radiation and essentially for β radiation. If required, the adherent and carrier layers with regard to their material and thickness may also be formed so thin so as to be transparent for α radiation, e.g. of 4 to 6 MeV, which requires layer thicknesses of clearly below 50 µm and densities of ≤1 g/cm³.

In an advantageous layer structure the adherent layer is formed on the skin surface prior to assembling the layer structure, the adherent layer being formed e.g. from a synthetic film sprayable onto the skin, in particular a liquid bandage on the basis of polyurethanes, polyacrylates, especially poly(butyl methacrylate, methyl methacrylate); or 2-octyl cyanoacrylate. Through this measure two problems can be solved at the same time: on the one hand, in covering the lesion with such a separate adherent layer, the lesion is closed on the surface, which also serves as protection against infections, and, on the other hand, the adherent layer is used for the alignment and fixation of the carrier layer. The transparency of adherent layer and carrier layer is of great advantage as the attending physician may recognize both the lesion and the skin markings for localizing the area to be treated through the layers.

Typical sprayed adherent layers have a thickness of 1 to 80 µm, particularly, 3 to 60 µm. Measurements of the thicknesses surprisingly revealed that the thickness of such sprayed adherent layers is comparatively constant and subject to merely minor deviations which are irrelevant therapeutically.

According to the layer structure in accordance with the invention, the adherent layer is located on the proximal side of the carrier layer.

Particularly in case of smaller and geometrically less demanding skin lesions a carrier layer that at the same time is an adherent layer has turned out to be of advantage, the carrier layer being formed as a self-adhering layer, e.g. in the manner of an adhesive foil coated on one side.

For the present invention carrier layers in form of foils are considered that have a thickness of 15 to 80 µm, particularly 20 to 60 µm, preferably 30 to 40 µm. Such carrier layers are sufficiently thin to essentially adapt to any complex geometry of a lesion such as, for example, in the helix area of an auricle, in the area of the eyes, or in the nasolabial fold as well as on outer and inner labia of the vulva and on the penis.

Preferred materials for the carrier layer foil are selected from the group consisting of: polyurethane foil, polyamide foil, polyolefin foil, in particular polyethylene and polypropylene foil. Those synthetic materials have the advantage of biocompatibility while being sterilizable and available at low costs at the same time. Moreover, in the layer thicknesses used in the layer structure in accordance with the invention, they allow the electrons of β radiation to pass through in a virtually unimpeded manner.

For removing the layer structure from the skin surface or from the adherent layer, respectively, it is advantageous if the carrier layer foil has at least one zone without adhesive force in its outer periphery. After termination of the treatment, the carrier layer foil may easily be removed there together with the emission layer and possibly a covering layer, using particular forceps, e.g. forceps in accordance with DE 20 2010 005 805 U1, and can be disposed of properly.

Typically, in the layer structure in accordance with the invention, the emission layer is a polymer matrix, preferably a water-based polyacrylate matrix. Such polymer matrices are known from the range of polyacrylate colors and therefore are available with all desired properties such as color, viscosity, processing time, curing temperature, etc. Moreover, they do not include organic solvents that might stress the patient and medical staff.

In accordance with a preferred embodiment, the layer structure of the present invention includes an emission layer containing a radionuclide selected from the group consisting of: β emitters, in particular $^{32}$P, $^{90}$Y, $^{166}$Ho, $^{177}$Lu, and $^{188}$Re.

Those radionuclides have proved to be very successful in the therapy of BCC and SCC and moreover are fairly readily available.

It turned out to be of particular advantage that the emission layer is a polyacrylate matrix including homogenously spread $^{188}$rhenium sulfide, e.g. $^{188}$Re$_2$S$_7$. The compound forms a colloid and thus ensures extremely homogenous distribution and stable dispersion at the same time, so that a homogenous source of radiation is available in the emission layer. At present, it has not yet been totally clarified as to whether rhenium sulfide is exclusively provided as Re$_2$S$_7$, or whether possibly further sulfides, also in mixed form, may be provided.

Therefore, for the purpose of the present invention, the formula $^{188}$Re$_2$S$_7$ also is to comprise possible further sulfides, also possible mixed sulfides, of rhenium, which thus likewise fall within the scope of protection of the present patent/application.

If required, the layer structure may be closed externally by a covering layer that is located distally on the emission layer, thereby closing the emission layer "in the manner of a sandwich" by the carrier layer and the covering layer. On the one hand, this measure safeguards further shielding for the medical staff and, on the other hand, prevents accidental contamination through restless and careless patients that may come into contact with the emission layer through incautious movements and thus may contaminate themselves and the nuclear medicine treatment unit.

Typically, the covering layer with regard to its consistency and thickness is formed such that it is impermeable to α, β and γ radiation emitted by the radionuclides of the emission layer.

Polyester, polyethylene or polypropylene foils or aluminum foils laminated with polyester, polyethylene or polypropylene have turned out to be advantageous materials for the covering layer, which preferably have a thickness of 100 to 200 μm.

Preferably, the covering layer is applied to the emission layer not fully cured and adheres to the emission layer after application.

With the radionuclides $^{32}$P, $^{90}$Y, $^{166}$Ho, $^{177}$Lu, and $^{188}$Re readily available β emitter are at hand. Thus, $^{188}$Re, for example, may be generated via a $^{188}$W/$^{188}$Re generator well known to a person skilled in the art. Moreover, $^{188}$Re has a comparatively short half-life of 16.7 h, so that accumulated radioactive waste abates rapidly and does not lead to problems with the disposal thereof.

The measure that the layer structure in accordance with the invention has a covering layer on the emission layer in a distal direction safeguards that the radionuclide containing emission layer is virtually self-contained, so that upon removal no radioactive contaminations are to be feared, neither on the side of the patients nor on the side of the medical staff.

A covering layer of polyester, polyethylene or polypropylene foil or else an aluminum foil laminated with polyester, polyethylene or polypropylene with thicknesses of 100-200 μm has turned out to be of particular advantage.

Further advantages and features of the present invention are to be seen from the description of an example.

EXAMPLE

Preparation of the Patient

Prior to treatment with the selected radionuclide, $^{188}$Re in the example, the lesion is to be examined by a dermatologist and the area to be treated is to be determined. This area is then marked with a pen pleasant to the skin. The surface of the marked area that is to be treated with the radioactive nuclide, has to be determined. This is done by computer-aided evaluation of a photograph or a scan of the marked area to be treated.

For treatment, the patient is brought into a position that for the most part makes horizontal application of the liquid matrix possible, so that it does not run. As a rule, the patient lies on a couch and moreover care has to be taken that the posture is comfortable to the patient since he/she has to remain in the position for 1-3 hours.

The β dose of radiation of the selected radionuclide, i.e. $^{188}$Re in this case, is computed using methods known per se.

Prior to the treatment, the skin lesion to be treated is to be cleaned and drained. Any possibly existing scab is to be removed carefully. Moreover, the lesion may not bleed or deliver secretions. In case bleedings occur, suitable hemostatic measures that are known per se are used.

A liquid bandage on the basis of polyurethane is directly applied to the skin lesion and the surrounding skin as adherent layer. Subsequently, one has to wait for a few seconds until no more solvents can be detected.

Measurements on such sprayed adherent layers have shown that they have a thickness in the range of 3-60 μm and, contrary to general expectations, exhibit comparatively little deviations in layer thickness.

A sterile, very thin, approximately 35 μm thick transparent medical polyurethane foil is applied to the skin portion with the adherent layer and is carefully pressed on. The polyurethane foil serves as a carrier layer. The carrier layer foil adheres to the adherent layer and is thus fixed. The substance and thickness in a two-digit μm range make it possible for the carrier foil to adapt to even complex geometrical lesions, such as on the edge of the Helix auriculae or in the nasolabial fold, in a crease-free manner while ensuring at the same time that the distance of the surface of the lesion to the (patient-side) proximal side of the emission layer is essentially equal. This ensures an equal dose of radiation for all areas of the lesion to be treated.

The carrier layer foil is adhered to the skin such that loose areas exist on the edge that are not tied to the adherent layer, so that the carrier layer foil later may be grabbed with the aid of specifically configured forceps (such as the tool described in German utility model DE 20 2010 005 805 U1) and the overall layer structure may be removed from the adherent layer and hence the lesion. The carrier layer should be considerably larger than the lesion, so that the skin around is completely covered by the foil.

Preparation of the Treatment

The radioactive agent, $^{188}$Re in the present case, is delivered from a corresponding plant of nuclear physics in a so-called carpule designed as disposable article and loaded with a volume of 0.3 ml each, with activities of up to 2.2 GBq per carpule at the time of supply to the hospital. Due to the fairly low half-life of $^{188}$Re of about 16.7 hours the manufacturer correspondingly has to calibrate higher so as to ensure the amounts of radioactivity on the application site.

Delivery is effected in a shielded transport container and the carpules are taken only shortly before the application. The carpule itself contains $^{188}$Re in form of a $^{188}$Re$_2$S$_7$ as a dispersion in an acrylate-water-TiO$_2$-based matrix suspension as colloid having an average particle diameter of approximately 500 nm in the present example.

Prior to withdrawal of the radioactive mixture from the carpule the carpule is again mixed. For this purpose, the carpule contains a mixing element made of metal which being driven from outside is moved up and down within the carpule, so that all components of the matrix, particularly the TiO$_2$ and the $^{188}$Re particles, are mixed with each other.

Subsequently, an applicator in accordance with DE102009054388 known per se is loaded with each carpule. The next step includes the determination of the actual amount of radioactivity contained in the loaded carpule at the time of application. The activity at the time of application is determined via a simple subtraction method (measurement of the activity of the carpule prior to the treatment, same measurement after the treatment, the resulting activity of the measurement of the difference thus was used for treating the patient and his/her lesion).

In particular, the applicator with inserted carpule is measured in a specific activimeter. In the example, the activimeter is a specific well-type ionization chamber of MED Medizintechnik Dresden GmbH. After the measurement, applicator and carpule are ready for the treatment.

Treatment—Application of the Emission Layer Matrix

The carpule is activated for treatment in that the head of the carpule is pressed with the applicator. The carpule is thus pushed together and a needle pierces through the diaphragm which previously retained the radioactive contents.

After removing the sheath from the carpule, treatment may start. The attending physician spreads the carrier layer foil over the skin in the previously marked area of the skin lesion with the polyacrylate matrix, so that the whole area is covered uniformly to thereby form the emission layer that contains the $^{188}$Re$_2$S$_7$. The applicator is formed in two parts, one part being formed as a thick pen so as to be easy to handle. Moreover, a hand shield is provided which protects the physician against radioactive radiation. Dosage of the matrix and the radioactive amount is done via the second part of the applicator.

The viscous $^{188}$rhenium-containing polyacrylate matrix of the emission layer hardens within 10 to 20 minutes without shrinking essentially. Subsequently to the application of the emission layer, a polyester-laminated aluminum foil having a thickness of approximately 100 μm is applied onto the still slightly wet emission layer on the distal side thereof, which thus adheres to the polyacrylate matrix.

When the surface to be treated was covered and the application is terminated, the sheath is put on the carpule again. Afterwards, the activity of the carpule in the applicator is again determined with the aid of the above-indicated specific activimeter. The applied radioactive quantity of $^{188}$Re may be determined from the difference of the activity measurements. With the activity applied and the covered area the length of the treatment may be calculated. As a rule, the length of the treatment is between 1 and 3 hours.

Tables 1 to 4 serve as guidance for the length of the treatment as a function of the surface of the skin area to be treated.

TABLE 1

Application time on the basis of an energy dose of 50 Gy for a required penetration depth of 300 μm

| Treatment area [cm$^2$] | Specific radioactivity [MBq/cm$^2$] | Irradiation time [min] |
|---|---|---|
| 1 | 74 | 43 |
| 3 | 74 | 40 |
| 10 | 74 | 38 |

TABLE 2

Application time on the basis of an energy dose of 50 Gy for a required penetration depth of 400 μm

| Treatment area [cm$^2$] | Specific radioactivity [MBq/cm$^2$] | Irradiation time [min] |
|---|---|---|
| 1 | 74 | 49 |
| 3 | 74 | 45 |
| 10 | 74 | 43 |

TABLE 3

Application time on the basis of an energy dose of 50 Gy for a required penetration depth of 500 μm

| Treatment area [cm$^2$] | Specific radioactivity [MBq/cm$^2$] | Irradiation time [min] |
|---|---|---|
| 1 | 74 | 55 |
| 3 | 74 | 50 |
| 10 | 74 | 48 |

TABLE 4

Application time on the basis of an energy dose of 50 Gy for a required penetration depth of 600 μm

| Treatment area [cm$^2$] | Specific radioactivity [MBq/cm$^2$] | Irradiation time [min] |
|---|---|---|
| 1 | 74 | 61 |
| 3 | 74 | 55 |
| 10 | 74 | 53 |

In treating large lesions it has turned out that for the purpose of a minimum radiation exposure of the patient and efficient treatment at the same time it is sufficient to reduce the treatment times as compared to smaller areas to be treated. As is to be seen from the above tables 1 to 4, a reduction of the irradiation time by approximately 12% in a lesion with a surface of about 10 cm$^2$ as compared to one with only 1 cm$^2$ has turned out to be favorable.

In the example of a skin lesion with a surface of approximately 3 cm$^2$ diagnosed histologically as basal-cell carcinoma of the nasolabial area, the length of the treatment was approximately 55 minutes (energy dose of 50 Gy for a penetration depth of 600 μm, specific radioactivity [MBq/cm$^2$]$^{188}$Re, the applied volume was approximately 30 μl).

After the application, the carpule is disposed of in a suitable shielded waste container. Due to the low half-life of 16.7 hours the radioactivity of the $^{188}$Re abates within approximately 10 days.

Removal of the Emission Layer

After a length of treatment of 55 minutes the carrier layer foil on the skin lesion with the applied and meanwhile dried-up emission layer which was provided with a covering foil, is peeled off the skin of the patient using long forceps and subsequently is disposed of in a shielded waste container.

The patient's skin is cleaned after treatment and examined for radiating residues.

On account of the layer structure in accordance with the invention consisting of adherent layer—carrier layer—emission layer and in the example an additional covering layer, radioactive contamination was detected in none of approximately 500 cases of treatment.

As a possible side effect a slight rush of the treated area could be observed in some patients. After examinations after 2, 4 and 12 weeks and subsequently within a time lag of six months, 85% of the cases were cured without requiring further treatment.

Merely in a few cases it was necessary to perform a second and—very rarely—a third follow-up treatment, which then all led to success.

Follow-up studies of up to 44 months after the first treatment showed a cure of BCC and SCC of 85 to 90%.

The invention claimed is:

1. A layer structure for epidermal radionuclide therapy of a patient, comprising:
    a proximal adherent layer adapted for application of the layer structure on a patient's skin surface, the adherent layer comprised of a synthetic film sprayable onto the skin surface, the adherent layer excluding a skin gel;
    a flexible, transparent carrier layer located in a distal direction on top of the adherent layer, wherein the adherent layer is located on a proximal side of the carrier layer, and the carrier layer having an outer periphery with at least one zone without adhesive, wherein the carrier layer consists of a single layer, free from enclosure and is applied directly on top of the adherent layer without an intermittent layer; and
    an emission layer located on the carrier layer wherein the emission layer contains at least one radionuclide selected from a group consisting of $^{32}$P, $^{90}$Y, $^{166}$Ho, $^{177}$Lu, and $^{188}$Re,
wherein the adherent layer and the carrier layer with regard to their components and thicknesses are formed such that they are essentially transparent for α, β and γ radiation, and further wherein the adherent layer is sprayable onto the skin surface on the proximal side of the carrier layer prior to an assembling of the layer structure,
wherein the synthetic film is formed of a liquid bandage including polyurethanes and/or polyacrylates;
wherein the carrier layer is selected from the group consisting of polyurethane foil and polyamide foil, and wherein the emission layer is a water-based polyacrylate matrix including homogenously spread $^{188}$rhenium sulfide.

2. The layer structure according to claim 1, wherein the adherent layer has a thickness of 1 to 80 μm.

3. The layer structure according to claim 1, wherein the carrier layer further includes an adherent layer, the carrier layer being formed as a self-adhering layer.

4. The layer structure according to claim 1, wherein the carrier layer is formed as a foil having a thickness of 15 to 80 μm.

5. The layer structure according to claim 1, wherein the emission layer distally has a covering layer.

6. The layer structure according to claim 5, wherein the covering layer with regard to its consistency and thickness is formed such that the covering layer is essentially impermeable to the α, β and γ radiation emitted by the at least one radionuclide of the emission layer.

7. The layer structure according to claim 6, wherein the covering layer is polyester or polypropylene or an aluminum foil laminated with polyester, polyethylene or polypropylene which has a thickness of 100 to 200 μm.

8. The layer structure according to claim 1, wherein the emission layer further comprises $^{188}$Re$_2$S$_7$ as a dispersion.

9. A method of applying a layer structure for epidermal radionuclide therapy of a patient, comprising:
    applying a proximal adherent layer on a patient's skin surface to be treated, the adherent layer comprised of a synthetic film sprayable onto the skin surface, the adherent layer excluding a skin gel;
    applying a flexible, transparent carrier layer in a distal direction on the adherent layer, wherein the adherent layer is located on a proximal side of the carrier layer, and the carrier layer having an outer periphery with at least one zone without adhesive wherein the carrier layer consists of a single layer, free from enclosure and is applied directly on top of the adherent layer without an intermittent layer; and
    applying at least one radionuclide-containing emission layer located on the carrier layer wherein the radionuclide is selected from a group consisting of $^{32}$P, $^{90}$Y, $^{166}$Ho, $^{177}$Lu, and $^{188}$Re,
wherein the adherent layer and the carrier layer with regard to their components and thickness are formed such that they are essentially transparent for α, β and γ radiation, wherein the adherent layer is formed on the skin surface prior to applying the carrier layer.

10. The method according to claim 9, wherein the sprayable synthetic film is formed of a liquid bandage consisting of polyurethanes or polyacrylates.

* * * * *